United States Patent [19]

Okawa

[11] Patent Number: 5,166,414

[45] Date of Patent: Nov. 24, 1992

[54] PROCESS FOR PRODUCING ISOCYANATE COMPOUND

[75] Inventor: Takashi Okawa, Niigata, Japan

[73] Assignee: Mitsubishi Gas Chemical Company, Inc., Tokyo, Japan

[21] Appl. No.: 744,734

[22] Filed: Aug. 14, 1991

Related U.S. Application Data

[63] Continuation-in-part of Ser. No. 606,977, Oct. 31, 1990, abandoned.

[30] Foreign Application Priority Data

Dec. 28, 1989 [JP] Japan .................................. 1-338286

[51] Int. Cl.$^5$ ............................................ C07C 263/00
[52] U.S. Cl. ........................................................ 560/345
[58] Field of Search ..................................... 560/24, 345

[56] References Cited

U.S. PATENT DOCUMENTS 3,277,140 10/1966 Donovan et al. .

4,100,351 7/1978 Romano et al. ........................ 560/24
4,258,200 3/1981 Daughenbaugh ..................... 560/24

FOREIGN PATENT DOCUMENTS 323514 1/1988 . European Pat. Off. .

*Primary Examiner*—Alan Siegel
*Attorney, Agent, or Firm*—Armstrong & Kubovcik

[57] ABSTRACT

There is disclosed a process for producing an isocyanate compound from a formamide compound or an amine compound which comprises (a) the first reaction step of reacting a formamide compound with dimethyl carbonate in the presence of an alkali catalyst, or reacting methyl formate and an amine compound with dimethyl carbonate in the presence of an alkali catalyst, to produce a corresponding urethane compound, and (b) the second reaction step of thermally decomposing the urethane compound at a temperature of 150°–350° C. and separately recovering the methanol and the corresponding isocyanate compound thus formed.

9 Claims, No Drawings

PROCESS FOR PRODUCING ISOCYANATE COMPOUND

This is a continuation-in-Part application based on the application of Ser. No. 07/606977 filed on Oct. 31, 1990 now abandoned.

BACKGROUND OF THE INVENTION

The present invention relates to a process for producing isocyanate compounds which comprises producing a urethane compound from a formamide compound, or an amine compound, and dimethyl carbonate used as starting materials, followed by thermal decomposition thereof.

Isocyanate compounds, particularly those which have two isocyanate groups in the molecule, are useful as a starting material for polyurethane, polyurea, etc.

Isocyanate compounds are presently produced commercially by the reaction of a primary amine compound with phosgene. The phosgene process currently in use has difficulties in the handling of highly poisonous phosgene, disposal of hydrochloric acid, corrosion of equipment, etc., so that an industrially feasible production process which can replace it is eagerly desired. In recent years, with such a situation as the background, various processes which use no poisonous phosgene have been proposed.

Processes for producing an isocyanate compound which use no phosgene may be divided, when classified according to the principal starting materials, into those which use a formamide compound, amine compound and nitro compound, respectively. When classified according to the reaction steps, they may be divided into a process wherein an isocyanate compound is directly obtained by one-step reaction and a process for producing an isocyanate by two-step reaction wherein a urethane compound is produced first and then it is thermally decomposed.

The processes which use a formamide compound as the principal starting material include processes wherein isocyanates are directly obtained by dehydrogenation. U.S. Pat. No. 3,960,914 discloses a process which comprises dehydrogenating a formamide compound in a nonaqueous solvent with the aid of a catalyst of a platinum group element such as Pd, but the process has drawbacks of a low reaction rate and a selectivity toward isocyanate compounds of as low as 30%. U.S. Pat. No. 4,207,251 discloses a process comprising subjecting a formamide compound to a gas phase oxidative dehydrogenation for a specified contact time in the presence of Ag-containing catalyst, but the process is of little practical utility, the yield of isocyanate compounds being as low as 21% according to the working examples shown therein. U.S. Pat. No. 3,277,140 discloses a process comprising reacting a formamide compound with halogen such as bromine in the presence of a heterocyclic nitrogen compound, but the process gives an insufficient yield of isocyanate compound and consumes 4 moles of the heterocyclic compound as its halide per 1 mole of the isocyanate compound formed, and is hence economically unfavorable.

On the other hand, U.S. Pat. No. 4,661,217 discloses a process comprising oxidizing a formamide compound on a graphite electrode with NaBr used as the supporting electrolyte in an alcohol solvent to prepare a corresponding urethane compound. Since the urethane compound thus obtained can be converted into an isocyanate compound by thermal decomposition, there is suggested a possibility that a non-phosgene process which uses a formamide compound as a starting material can be developed. However, upon investigation of the urethane synthesis step of said process, it has been revealed that though a relatively high urethane yield is obtained a severe deterioration of the electrode takes place, so that the process has a difficulty in being put into practice in a commercial scale apparatus.

On the other hand, processes are known which produce urethane compounds from amine compounds and dimethyl carbonate (U.S. Pat. No. 3,763,217, E.P. No. 48,371, U.S. Pat. No. 4,395,565). These processes comprise reacting an amine compound with dimethyl carbonate in the presence of a Lewis acid catalyst, lead-, titanium- or zirconium-based catalyst, alkali catalyst, etc. According to the working examples shown therein, however, the processes generally have drawbacks of giving a low rate of reaction and being liable to form methylated compounds as by-products, leading to a low urethane yield. An improved process thereof has also been proposed, noticing the fact that specific amine compounds undergo the methylation of side reaction with difficulty, which comprises using dimethyl carbonate with a water content of less than 0.2% and adding the amine compound and sodium methylate catalyst thereto continuously or intermittently (PCT WO 88/05430).

The object of the present invention is to provide a process for producing an isocyanate compound economically and efficiently by using a formamide compound or an amine compound as a principal starting material and without using poisonous phosgene.

SUMMARY OF THE INVENTION

The present inventors have made extensive study to develop a process capable of producing an isocyanate compound from a formamide compound or an amine compound with a high yield and high space time yield. As a result, it has been found that by reacting a formamide compound with dimethyl carbonate in the presence of an alkali catalyst or reacting methyl formate and an amine compound with dimethyl carbonate in the presence of an alkali catalyst, a corresponding urethane compound can be obtained with a high reaction rate and a good yield, and further that by combining the above process with a thermal decomposition which converts the urethane compound thus obtained into an isocyanate compound, said object can be easily attained. The present invention has been accomplished on the basis of above finding.

Thus, according to the first aspect of the present invention, there is provided a process for producing an isocyanate compound from a formamide compound or an amine compound which comprises (a) the first reaction step of reacting a formamide compound with dimethyl carbonate in the presence of an alkali catalyst at a temperature of 0–150° C. to produce a corresponding urethane compound, and (b) the second reaction step of thermally decomposing said urethane compound at a temperature of 150–350° C. under a reduced pressure of 1–500 mmHg and without using a catalyst in an inert solvent having a higher boiling point than that of the isocyanate compound to be formed, and then subjecting the vapor mixture of methanol and the corresponding isocyanate compound thus formed to partial condensation.

Further, according to the second aspect of the present invention, there is also provided a process for producing an isocyanate compound from an amine compound which comprises (a) the first reaction step of reacting methyl formate and an amine compound with dimethyl carbonate in the presence of an alkali catalyst at a temperature of 0–150° C. to produce a corresponding urethane compound, and (b) the second reaction step of thermally decomposing said urethane compound at a temperature of 150–350° C. under a reduced pressure of 1–500 mmHg and without using a catalyst in an inert solvent having a higher boiling point than that of the isocyanate compound to be formed, and then subjecting the vapor mixture of methanol and the corresponding isocyanate compound thus formed to partial condensation.

DETAILED DESCRIPTION OF THE INVENTION

The first aspect of the present invention may be expressed by the following reaction formulas (1) and (2). In the first reaction step, a urethane compound and methyl formate are formed from a corresponding formamide compound and dimethyl carbonate. In the second reaction step, an isocyanate compound and methanol are formed from a corresponding urethane compound. In the first reaction step of the formula (1), a urethane compound can be obtained with a high reaction rate and a high yield merely by placing an alkali catalyst such as sodium methylate catalyst, a corresponding formamide compound and dimethyl carbonate collectively in a reactor and allowing the resulting mixture to react under reflux at normal pressure.

$$R(NHCOH)_n + nCO(OCH_3)_2 \xrightarrow{\text{alkali catalyst}} \quad (1)$$

$$R(NHCOOCH_3)_n + nHCOOCH_3$$

$$R(NHCOOCH_3)_n \xrightarrow{\text{Thermal decomposition}} R(NCO)_n + nCH_3OH \quad (2)$$

The formamide compound used in the first aspect of the present invention may be obtained by various methods, but is preferably prepared by the reaction of a corresponding amine compound with methyl formate as can be expressed by the following reaction formula (3). It is advantageous that the methyl formate used here can be provided by recycling the methyl formate formed in the first reaction step of the formula (1).

$$R(NH_2)_n + nHCOOCH_3 \xrightarrow{\text{Without catalyst}} R(NHCOH)_n + nCH_3OH \quad (3)$$

The above reaction is characterized in that it proceeds quantitatively and with a very high reaction rate simply by mixing an amine compound and methyl formate in the absence of a catalyst at normal temperature and normal pressure.

The process of the second aspect of the present invention comprises reactions expressed by the formulas (1)', (2)' and (3)'.

$$R(NH_2)_n + nHCOOCH_3 \xrightarrow{\text{Without catalyst}} R(NHCOH)_n + nCH_3OH \quad (1)'$$

$$R(NHCOH)_n + nCO(OCH_3)_2 \xrightarrow{\text{Alkali catalyst}} \quad (2)'$$

$$R(NHCOOCH_3)_n + nHCOOCH_3$$

$$R(NHCOOCH_3)_n \xrightarrow{\text{Thermal decomposition}} R(NCO)_n + nCH_3OH \quad (3)'$$

Thus, a urethane compound can be obtained with a high reaction rate and a high yield by reacting methyl formate and a corresponding amine compound with dimethyl carbonate in the presence of an alkali catalyst through an in situ method.

The reaction of forming a urethane compound and methanol from an amine compound and dimethyl carbonate is known already as described above (U.S. Pat. No. 3,763,217, E.P. No. 48,371, U.S. Pat. No. 4,395,565, PCT WO 88-05,430) and may be expressed by the following formula (4)'.

$$R(NH_2)_n + nCO(OCH_3)_2 \longrightarrow R(NHCOOCH_3)_n + nCH_3OH \quad (4)'$$

Upon tracing the components relating to the above reaction it was revealed that no formamide compound was recognized as the reaction intermediate.

On the other hand, according to the process of the second aspect of the present invention, based on the finding that the rate of reaction of the formula (1)' in the absence of catalyst and the rate of reaction of the formula (2)' in the presence of alkali catalyst are very high as already described above in relation to the first aspect of the present invention, a urethane compound is obtained with a very high reaction rate and a high yield through the reaction of the formula (2)' using as the reaction intermediate the formamide compound formed by the reaction of the formula (1)' and then an isocyanate compound is produced by the thermal decomposition thereof.

Some embodiments of the process of the present invention will be described in detail below.

The formamide compounds used as a principal starting material in the first aspect of the present invention may be classified into those of aromatic group and those of aliphatic group. Particularly preferably used among them in the first aspect of the present invention are aliphatic formamide compounds having two formamide groups. Aliphatic formamide compounds include, as classified according to the molecular structure, alicyclic formamide compounds and chain aliphatic formamide compounds. As specific examples of the starting materials corresponding to industrially useful isocyanate compounds, mention maybe made of N,N'-[1,3-phenylenebis(methylene)]bisformamide and the 1,4-isomer of the same structure, N,N'-[1,3-cyclohexylbis(methylene)]bisformamide and the 1,4-isomer of the same structure, 3-formamidomethyl-3,5,5-trimethyl-1-formamidocyclohexane, 1,6-hexamethylenediformamide, etc.

In the second aspect of the present invention, on the other hand, aliphatic amine compounds are preferably used as the principal starting material. Particularly advantageously used among them are m- and p-xylylenediamine, N,N'-[1,3-cyclohexylbis(methylene)]-bisamine and its 1,4-isomer.

While aliphatic diisocyanate compounds with a high added value can be obtained from these compounds, the process of the present invention makes it also possible to produce aromatic diisocyanate compounds with a high versatile utility from aromatic diamine compounds.

Dimethyl carbonate used as an auxiliary material and methyl formate used as an additive may be those on the market as they are or further purified as occasion demands. These starting materials preferably have a water content reduced to a possible minimum, in order to decrease the amount of catalyst and to maintain its activity.

The amount of dimethyl carbonate to be used in the process of the first aspect of the present invention is in the range of 1–20 moles, preferably 1–10 moles, per 1 mole of the formamide group of a formamide compound. When the amount used is less than 1 mole, unreacted formamide will remain. When it is more than 20 moles, the space time yield is low, which are unpractical. Similarly, when an amine compound is used as the principal starting material in the second aspect of the present invention, the amount of dimethyl carbonate to be used per 1 mole of the amino group is in the range of 1–20 moles, preferably 1–10 moles. The amount of methyl formate to be added is in the range of 0.1–5 moles, preferably 0.1–1 mole, relative to 1 mole of the amino group. When the amount used is less than 0.1 mole, the reaction promoting effect by methyl formate is small. When it is more than 5 moles, the space time yield will be low.

The alkali catalyst preferably used in the present invention is the alcoholate of an alkali metal or alkaline earth metal. Specific examples thereof include the methylates, ethylates or the like of sodium, potassium, lithium, calcium, barium, etc. In practical use, sodium methylate is preferable from the viewpoint of easy availability and economical advantage. Although the alkali catalyst may be used in the form of both solid and solution, the most preferable is the methanol solution of sodium methylate available on the market. The amount of alkali to be used in the first aspect of the present invention, in the case of sodium methylate, is in the range of 0.005–0.2, preferably 0.01–0.12, in a molar ratio to formamide. When the molar ratio used is less than 0.005, a sufficient reaction rate is not obtained, whereas when the molar ratio is more than 0.2 the cost of catalyst becomes too high, resulting in economical disadvantage.

The amount of methyl formate to be added in the second aspect of the present invention is in the range of 0.1–5 moles, preferably in the range of 0.1–1 mole, relative to 1 mole of the amino group. When the amount used is less than 0.1 mole the reaction promoting effect by methyl formate is small, whereas when it is larger than 5 moles the space-time yield is low.

As described above, the reaction of forming a urethane compound and methanol from an amine compound and dimethyl carbonate is already known, and sodium methylate is used as a catalyst in WO 88/05430. The second aspect of the present invention is featured in that the amount of an alkali catalyst can be greatly reduced by reacting methyl formate and an amine compound with dimethyl carbonate in the presence of an alkali catalyst. That is, by conducting the reaction (1)' and (2)' in the presence of methyl formate, the amount of the alkali catalyst can be greatly reduced, so that the catalyst expense can be lowered and burdens in neutralization of the reaction liquid by an acid, separation of salts and disposal thereof, etc. can be reduced. Thus, the process of the second aspect of the present invention is of great industrial advantage.

The amount of alkali to be used in the second aspect of the present invention, in the case of sodium methylate, is 0.005–0.05, preferably 0.01–0.03, in terms of the molar ratio relative to the starting amine compound. When the molar ratio of the alkali to the amine compound is too low, a sufficient reaction rate is not obtained, whereas when the ratio is too high, the catalyst cost becomes high and burdens in neutralization of the reaction liquid by an acid, separation of salts and disposal thereof, etc., increase, resulting in economical disadvantage.

When the principal starting material is a solid, or the urethane compound formed will deposit as a solid, in the reaction of the present invention, the reaction can advantageously be carried out by use of a solvent. The solvent should be inert to the starting material, catalyst, and urethane compound formed. Specific examples of solvents which can be used include alcohols such as methanol and ethanol, ethers such as tetrahydrofuran and dioxane, hydrocarbons such as benzene and toluene, and also sulfolane, etc. The solvent is advantageously used in a necessary minimum amount, usually in the range of 1–10 times by weight relative to the principal starting material.

The operations for the first reaction step are as follows. A formamide compound, dimethyl carbonate and alkali catalyst in the first aspect of the invention, or an amine compound, methyl formate, dimethyl carbonate and alkali catalyst in the second aspect of the present invention and, if necessary, a solvent are charged together into a reactor and allowed to react, whereby a urethane compound can be obtained with a sufficient reaction rate and a high yield. In the case of a batchwise reaction it is also possible, as occasion demands, to feed the alkali catalyst alone continuously or intermittently. Further, in the reaction of a formamide compound, dimethyl carbonate and alkali catalyst according to the first aspect of the present invention, it can also be favorably practiced to withdraw the methyl formate formed out of the system by reaction-distillation.

In the first reaction step, the reaction may be conducted at normal or applied pressure at a reaction temperature in the range of 0–150° C. Practically, however, it is preferably conducted under reflux at normal pressure at a reaction temperature in the range of 20–90° C.

The urethane compound formed can be recovered from the reaction liquid and further purified by various methods combining distillation, solvent extraction, washing, neutralization, crystallization, and other means. One example will be specifically shown below. Dimethyl carbonate, methyl formate and methanol are recovered from the reaction liquid by conventional evaporation or simple distillation under normal or reduced pressure. The evaporation concentrate thus obtained is dissolved in a hydrocarbon solvent such as benzene, toluene and xylylene, and then an aqueous acid solution is added thereto and stirred, to effect the neutralization of the alkali catalyst. The acids usable herein may be mineral acids, such as hydrochloric acid, sulfuric acid, nitric acid, and phosphoric acid. The neutralized solution separates into two layers. After separation of the aqueous layer, the organic layer containing the urethane compound is preferably further washed with water. From the organic layer the urethane compound can be recovered by solvent recovery by means of conventional evaporation or simple distillation, or by crystallization. Particularly when the urethane compound is solid at normal temperature, it is industrially practical to handle the urethane compound in the form of its solution through the technique of solvent exchange between the solvent of the organic layer and the high boiling point solvent used in the succeeding thermal decomposition step.

In the second reaction step, the urethane compound recovered and purified in the manner described above is thermally decomposed, whereby methanol and the intended isocyanate compound can be obtained. Preferably, said thermal decomposition is conducted in the absence of a catalyst in an inert solvent having a higher boiling point than that of the isocyanate compound to be formed, and the vapor mixture of methanol and the isocyanate compound evolved is subjected to partial condensation. In particular, although m- and p-xylylene diisocyanate, N,N'-[1,3-cyclohexylbis-(methylene)-bisisocyanate and the like are susceptible to polymerization and are difficultly obtained in a high yield by prior methods, such isocyanates also can be produced advantageously in a high yield according to the process of the present invention by conducting thermal decomposition in the absence of a catalyst in an inert solvent having a higher boiling point than that of the isocyanate compound to be formed and then subjecting the vapor mixture of methanol and the isocyanate compound thus formed to partial condensation. The solvent used here preferably shows a large boiling temperature difference, particularly preferably a temperature difference of 40° C. or more, to facilitate withdrawing the isocyanate compound formed by the thermal decomposition of the urethane compound selectively out of the system and separating it by condensation. Specific examples of preferred such solvents include esters such as dioctyl phthalate, didecyl phthalate, didodecyl phthalate and diphenyl phthalate; and aromatic hydrocarbons commonly used as a heating medium, such as dibenzyltoluene, pyrene, triphenylmethane, bromonaphthalene, phenylnaphthalene, and benzylnaphthalene. The amounts of these solvents used is 0.1-100 times by weight, preferably 0.5-50 times by weight, relative to the urethane compound.

The thermal decomposition of the urethane compound is conducted at a temperature in the range of 150-350° C., preferably 200-300° C. A temperature lower than 150° C. gives a low decomposition velocity, whereas a temperature higher than 350° C. increases the formation of by-products. The operation pressure should be a pressure at which methanol and the isocyanate compound can vaporize in correspondence to said decomposition temperature, and is usually in the range of 1-500 mmHg. Thus, the vapor mixture of methanol and the isocyanate compound formed by the thermal decomposition of the urethane compound is preferably withdrawn out of the system in the form of reaction-distillation. Then the components can be separated and recovered independently of each other by taking advantage of the difference between the condensing temperatures of the respective fractions.

The process of the present invention can favorably be performed both in a batch-wise operation and in a continuous operation.

According to the present invention, isocyanate compounds can be produced efficiently without handling highly poisonous phosgene.

In the process of the present invention, a urethane compound is produced from a formamide compound and dimethyl carbonate and in the first reaction step and then an isocyanate compound is produced by thermally decomposing the urethane compound in the second reaction step, with high yields obtained in both reaction steps.

In the process of the second aspect of the present invention, in which a urethane compound is produced from an amine compound, methyl formate and dimethyl carbonate in the first reaction step, a high reaction rate can be obtained and hence the space time yield is also high; further, by said addition of methyl formate the amount of alkali catalyst used can be greatly reduced and burdens in neutralization of the reaction liquid, separation of salts and disposal thereof, etc. can also be lowered. Thus, the process is highly excellent industrially.

In the second reaction step, further, by thermally decomposing a urethane compound in an inert solvent having a high boiling point without using a catalyst and then subjecting the vapor mixture of methanol and an isocyanate compound evolved to partial condensation, such isocyanates susceptible to polymerization can be produced from a starting material such as m- and p-xylylenediamine and N,N'-[1,3-cyclohexylbis(methylene)]bisamine in a high yield and with industrial advantage.

DESCRIPTION OF THE PREFERRED EMBODIMENTS

The present invention will be described further in detail below with reference to Examples.

Referential Example: Synthesis of Formamide Compound

Into a 1000-ml round-bottomed flask equipped with a stirrer were charged 200 g of m-xylylenediamine and 300 g of methanol, which was then placed in an ice-water mixture bath. Then 212 g of methyl formate was charged dropwise into the flask over a period of 10 minutes and then stirred for about 10 minutes. The flask was then transferred to a rotary evaporator and the whole amounts of methyl formate and methanol were recovered in a hot water bath (70° C.) under normal pressure and then under reduced pressure to obtain white crystals. After drying, the resulting product, weighing 281 g, was subjected to NMR analysis, IR analysis, elementary analysis and liquid chromatographic analysis and was identified as N,N'-[1,3-phenylenebis-(methylene)]bisformamide. The yield was confirmed to be 99.6%.

THE FIRST REACTION STEP. URETHANE SYNTHESIS EXPERIMENT

EXAMPLE 1

Into a 200 ml three-necked flask equipped with a reflux condenser, thermometer and stirrer were charged collectively 20 g of N,N'-[1,3-phenylenebis(methylene)]-bisformamide (hereinafter referred to a meta-xylylenediformamide), 60 g of dimethyl carbonate, and 2 g of a 22.5% methanol solution of sodium methylate, and the flask was placed in a water bath. The temperature of the water bath was elevated to 70° C. and then the charged mixture was allowed to react under reflux for 1 hour.

After the reaction, the resulting reaction liquid was analyzed by liquid chromatography and gas chromatography (using an internal standard method). Resultantly it was found that methyl N,N'-[1,3-phenylene-bis(methylene)]biscarbamate (hereinafter referred to as meta-xylylene dicarbamate) had been formed in 96.6% yield based on meta-xylylenediformamide. It was confirmed that the selectivity for meta-xylylene dicarbamate based on dimethyl carbonate was 98.2% and an amount of methyl formate corresponding to reacted meta-xylylenediformamide had been formed.

EXAMPLE 2

A 200-ml three-necked flask equipped with a fractionating column fitted with reflux condenser, a thermometer, and a stirrer was used as a reactor. The reactor was charged collectively with 20 g of meta-xylylenediformamide, 60 g of dimethyl carbonate and 1 g of a 22.5% methanol solution of sodium methylate and placed in a water bath. The temperature of the water bath was elevated to 70° C. and then the charged mixture was allowed to react for 30 minutes. During the time the distillate was collected from the fractionating column to a receiver through reaction-distillation.

After the reaction, the resulting reaction liquid and the distillate were analyzed by liquid chromatography and gas chromatography. Resultantly, the yield of meta-xylylene dicarbamate based on meta-xylylenediformamide was found to be 95.5%.

EXAMPLE 3

The same reactor as that used in Example 1 was charged collectively with 30 g of meta-xylylenediformamide, 60 g of dimethyl carbonate, 20 g of methanol, and 2 g of a 22.5% methanol solution of sodium methylate and then the reactor was placed in a water bath. The temperature of the water bath was elevated to 70° C. and then the charged mixture was allowed to react under reflux for 1 hour.

After the reaction the resulting reaction liquid was analyzed by liquid chromatography and gas chromatography. Resultantly, the yield of meta-xylylene dicarbamate based on meta-xylylenediformamide was found to be 96.8%.

EXAMPLE 4

A 500-ml three-necked flask equipped with a reflux condenser, thermometer and stirrer was charged collectively with 60 g of meta-xylylenediformamide and 180 g of dimethyl carbonate, and the flask was placed in a water bath. The temperature of the water bath was elevated to 60° C., then 2 g of a 22.5% methanol solution of sodium methylate was fed continuously to the flask over a period of 30 minutes, and the resulting mixture was allowed to react under reflux for 30 minutes.

After the reaction the resulting reaction liquid was analyzed by liquid chromatography and gas chromatography. Resultantly it was found that the yield of meta-xylylene dicarbamate based on meta-xylylenediformamide was 98.9%.

EXAMPLE 5

The same reactor as that used in Example 1 was charged collectively with 21 g of N,N'-[1,3-cyclohexyl-bis-(methylene)]bisformamide, 60 g of dimethyl carbonate, and 2 g of a 22.5% methanol solution of sodium methylate, and the reactor was placed in a water bath. The temperature of the water bath was elevated to 70° C. and then the charged mixture was allowed to react for 1 hour.

After the reaction, the resulting reaction liquid was neutralized with phosphoric acid and then analyzed by gas chromatography. Resultantly it was found that methyl N,N'-[1,3-cyclohexylbis(methylene)]-biscarbamate has been formed in 96.9% yield based on the formamide compound of the starting material. It was confirmed that the selectivity for urethane compound based on dimethyl carbonate was 97.8% and an amount of methyl formate corresponding to the reacted formamide compound had been formed.

EXAMPLE 6

The same reactor as that used in Example 2 was charged collectively with 18 g of 1,6-hexamethylenediformamide, 60 g of dimethyl carbonate, and 1 g of a 22.5% methanol solution of sodium methylate, and the reactor was placed in a water bath. The temperature of the bath was elevated to 70° C. and the charged mixture was then allowed to react for 1 hour. During the time, the distillate from the fractionating column was collected to a receiver through reaction-distillation.

After the reaction the resulting reaction liquid was neutralized with phosphoric acid and then analyzed by gas chromatography. Resultantly, the yield of methyl 1,6-hexamethylenedicarbamate was found to be 93.6% based on the starting formamide compound.

EXAMPLE 7

A 500-ml three-necked flask equipped with a reflux condenser, thermometer and stirrer was charged collectively with 40 g of meta-xylylenediamine, 198 g of dimethyl carbonate, 35 g of methyl formate and 0.70 g of a 22.5% methanol solution of sodium methylate, and the flask was placed in a water bath. The temperature of the water bath was elevated to 70° C. and the mixture was allowed to react under reflux for 3 hours.

After the reaction the resulting reaction liquid was analyzed by liquid chromatography and gas chromatography using an internal standard. Resultantly it was found that meta-xylylene dicarbamate was formed in 98.4% yield based on meta-xylylenediamine.

COMPARATIVE EXAMPLE 1

The same procedures as in Example 7 were followed except that no methyl formate was added. The yield of meta-xylylene dicarbamate obtained was 0.64% based on meta-xylylenediamine.

EXAMPLE 8

The same procedures as in Example 7 were followed except that 1.4 g of the 22.5% methanol solution of sodium methylate was used. The yield of meta-xylylene dicarbamate was 98.7% based on meta-xylylenediamine.

COMPARATIVE EXAMPLE 2

The same procedures as in Example 8 were followed except that no methyl formate was added. The yield of meta-xylylene dicarbamate obtained was 79.3% based on meta-xylylenediamine.

EXAMPLE 9

The same reactor that used in Example 1 was charged collectively with 15 g of N,N'-[1,3-cyclohexyl(methylene)]bisamine, 60 g of dimethyl carbonate, 4 g of methyl formate, and 0.5 g of a 22.5% methanol solution of sodium methylate, and the reactor was placed in a water bath. The temperature of the water bath was elevated to 70° C. and then the charged mixture was allowed to react for 3 hours.

After the reaction the resulting reaction liquid was neutralized with phosphoric acid and then analyzed by gas chromatography. Resultantly, the yield of methyl N,N'-[1,3-cyclohexylbis(methylene)]bis-carbamate was found to be 95.2% based on the starting amine compound.

THE SECOND REACTION STEP. URETHANE DECOMPOSITION EXPERIMENT

EXAMPLE 10

A 300-ml three-necked round-bottomed flask equipped with a capillary, thermometer and fractionating column fitted with a reflux condenser was used as a reactor. A receiver for collecting the downflow liquid was attached to the fractionating column. Hot water at 60° C. was passed through the reflux condenser. The upper parts of the reflux condenser and the receiver were connected to a vacuum line through a cold trap cooled with a methanol-dry ice mixture.

The reactor was charged with 20 g of meta-xylylene dicarbamate and 200 g of Marurotherm S solvent (major component: dibenzyltoluene), and was placed in a silicone oil bath. The atmosphere in the reaction system was replaced with nitrogen, then evacuated to a degree of vacuum of 25 mmHg, and the temperature in the flask was raised up to 260° C. Said conditions were maintained for 3 hours, and the evolved vapor was partially condensed and recovered by making use of the temperature difference between the reflux condenser and the cold trap.

After completion of the thermal decomposition, the liquids in the reactor, receiver, and cold trap were respectively analyzed by liquid chromatography and gas chromatography. Resultantly it was revealed that, at a conversion of meta-xylylene dicarbamate of 99.2%, the yield of meta-xylylene diisocyanate was 84.1% and the yield including that for the monoisocyanate of an intermediate was 97.2%.

EXAMPLE 11

The thermal decomposition of a urethane compound was conducted in the same manner as in Example 10 but by charging 20 g of meta-xylylene dicarbamate and 150 g of dioctyl phthalate and under conditions of 30 mmHg and 270° C. for 2.5 hours. Resultantly, the yield of meta-xylylene diisocyanate was 77.2% based on meta-xylylene dicarbamate and the yield including that for monoisocyanate was 86.2%. No unreacted meta-xylylene dicarbamate of the starting material was recognized in the reactor.

COMPARATIVE EXAMPLE 3

The same apparatus as that used in Example 10 was charged with 20 g of meta-xylylene dicarbamate, 200 g of Marurotherm S solvent and 0.1 g of manganese acetate tetrahydrate, and the thermal decomposition of urethane was conducted under conditions of 25 mmHg and a temperature of 250° C. It was found that foaming occurred 30 minutes after the initiation of thermal decomposition and that the reactants in the flask polymerized and no meta-xylylene diisocyanate was obtained.

COMPARATIVE EXAMPLE 4

The thermal decomposition of meta-xylylene diisocyanate was conducted in the same manner as in Example 10 except that 0.1 g of MnO$_2$ catalyst was used.

Resultantly, at a conversion of meta-xylylene carbamate of 92.0%, the yield of meta-xylylene diisocyanate was 29.1% and the yield including that for the monoisocyanate was 39.8%. After the reaction, polymer was found adhering to the wall of the flask, the surface of the thermometer, etc.

What is claimed is:

1. A process for producing an isocyanate compound from a formamide compound which comprises
   (a) a first reaction step of reacting a formamide compound with dimethyl carbonate in the presence of an alkali catalyst at a temperature of 0–150° C. to produce a corresponding urethane compound, and
   (b) a second reaction step of thermally decomposing the urethane compound at a temperature of 150–350° C. under a reduced pressure of 1–500 mmHg and without using a catalyst in an inert solvent having a higher boiling point than that of the isocyanate compound to be formed, and then subjecting the vapor mixture of methanol and the corresponding isocyanate compound thus formed to partial condensation.

2. A process for producing an isocyanate compound according to claim 1 wherein the formamide compound is an aliphatic formamide compound.

3. A process for producing an isocyanate compound according to claim 1 wherein the formamide compound is N,N'-[1,3-phenylenebis(methylene)]bisformamide or N,N'-[1,3-cyclohexylbis(methylene)]bisformamide.

4. A process for producing an isocyanate compound according to claim 1 wherein the alkali catalyst is sodium methylate.

5. A process for producing an isocyanate compound from an amine compound which comprises
   (a) a first reaction step of reacting methyl formate and an amine compound with dimethyl carbonate in the presence of an alkali catalyst at a temperature of 0–150° C. to produce a corresponding urethane compound, and
   (b) a second reaction step of thermally decomposing the urethane compound at a temperature of 150–350° C. under a reduced pressure of 1–500 mmHg and without using a catalyst in an inert solvent having a higher boiling point than that of the isocyanate compound to be formed, and then subjecting the vapor mixture of methanol and the corresponding isocyanate compound thus formed to partial condensation.

6. A process for producing an isocyanate compound according to claim 5 wherein the amine compound is an aliphatic amine compound.

7. A process for producing an isocyanate compound according to claim 5 wherein the amine compound is m-xylylenediamine or N,N'-[1,3-cyclohexylbis(methylene)]bisamine.

8. A process for producing an isocyanate compound according to claim 5 wherein the alkali catalyst is sodium methylate.

9. A process for producing an isocyanate compound according to claim 8 wherein the molar ratio of sodium methylate to the amine compound is 0.005–0.05.

* * * * *